(12) United States Patent
Gandee

(10) Patent No.: US 11,584,946 B2
(45) Date of Patent: Feb. 21, 2023

(54) BASELINE TESTING, ANALYSIS AND TREATMENT OF AN ENVIRONMENT

(71) Applicant: Gregory M. Gandee, Alexandria, VA (US)

(72) Inventor: Gregory M. Gandee, Alexandria, VA (US)

( * ) Notice: Subject to any disclaimer, the term of this patent is extended or adjusted under 35 U.S.C. 154(b) by 338 days.

(21) Appl. No.: 16/387,185

(22) Filed: Apr. 17, 2019

(65) Prior Publication Data

US 2019/0241930 A1 Aug. 8, 2019

Related U.S. Application Data

(63) Continuation of application No. 15/457,157, filed on Mar. 13, 2017, now abandoned.

(60) Provisional application No. 62/307,152, filed on Mar. 11, 2016.

(51) Int. Cl.
*C12Q 1/04* (2006.01)
*A61L 9/14* (2006.01)
*A01N 59/00* (2006.01)

(52) U.S. Cl.
CPC ............. *C12Q 1/04* (2013.01); *A01N 59/00* (2013.01); *A61L 9/14* (2013.01)

(58) Field of Classification Search
CPC .............. C12Q 1/04; A01N 59/00; A61L 9/14
See application file for complete search history.

(56) References Cited

U.S. PATENT DOCUMENTS 5,767,055 A 6/1998 Choy et al.
7,445,800 B2 11/2008 Morris et al.

OTHER PUBLICATIONS

Anonymous. Room Sizes; architectureCAD, downloaded from: http://www2.d125.org/im/ACAD/pdf/room_sizes.pdf (Year: 2012).*
Anonymous. Recommended Best Practices for Mold Investigation in Minnesota Schools; Enrironmental Health Division, Indoor Air Unit downloaded from: http://www.health.state.mn.us/communities/enrironment/air/docs/schools/investigations.pdf (Year: 2014).*
Anonymous. Causes, Detection, and Prevention of Mold and Mildew on Textiles; Conserve O Gram; downloaded from: http://www.nps.gov/museum/publications/conserveogram/16-01.pdf (Year: 1993).*
Cheong et al. Airborne Fungal Levels in an Australian Residential Home With Extensive Visible Mould Growth Pre and Post Remediation; 17th International Clean Air Environment Conference, Hobard, Australia, May, pp. 1-5 (Year 2005).
Crawford, G. Spore Migration in the Indoor Environment; AIHCE Roundtable 202, pp. 1-34, downloaded from https://www.aiha.org/aihce07/handouts/rt202crawford.pdf on Apr. 13, 2018. (Year 2007).
Razmovski et al. Adhesive Tapes as Capturing Surfaces in Burkard Sampling; Grana, vol. 37, pp. 305-310. (Year 1998).
Kiura et al. Bacteriocidal Activity of Electrolyzed Acid Water From Solution Containing Sodium Chloride at Low Concentration, in Comparison With That at High Concentration; Journal of Microbiological Methods, vol. 49, pp. 285-293. (Year 2002).
Anonymous. Wideband Integrated Bioaerosol Spectrometer (WIBS-4A) Operator Manual; Droplet Measurement Technologies, DOC-0345 Revision A-2, pp. 1-45. (Year 2013).
Gromicko et al. Air Sampling for Mold Inspections; InterNACHI, pp. 1-5, downloaded from https://web.archive.org/web/2014820212722/ https://www.nachi.org/air-sampling-mold-inspection.htm on Apr. 5, 2018 (Year 2014).
Office action dated Dec. 17, 2018 in parent U.S. Appl. No. 15/457,157.
Office action dated Aug. 24, 2018 in parent U.S. Appl. No. 15/457,157.

* cited by examiner

*Primary Examiner* — Melissa L Fisher
*Assistant Examiner* — Paul C Martin
(74) *Attorney, Agent, or Firm* — FisherBroyles LLP; Ian R. Walsworth

(57) ABSTRACT

The present disclosure relates to testing, analysis and treatment of an environment, wherein one or more baseline(s) is established for the environment. Systems and methods for detecting, treating, comparing and testing for mold, mold spores and mold fragments physically present or in the air of an environment are disclosed herein, as well as methods for remediating the effects of mold in the environment.

15 Claims, 1 Drawing Sheet

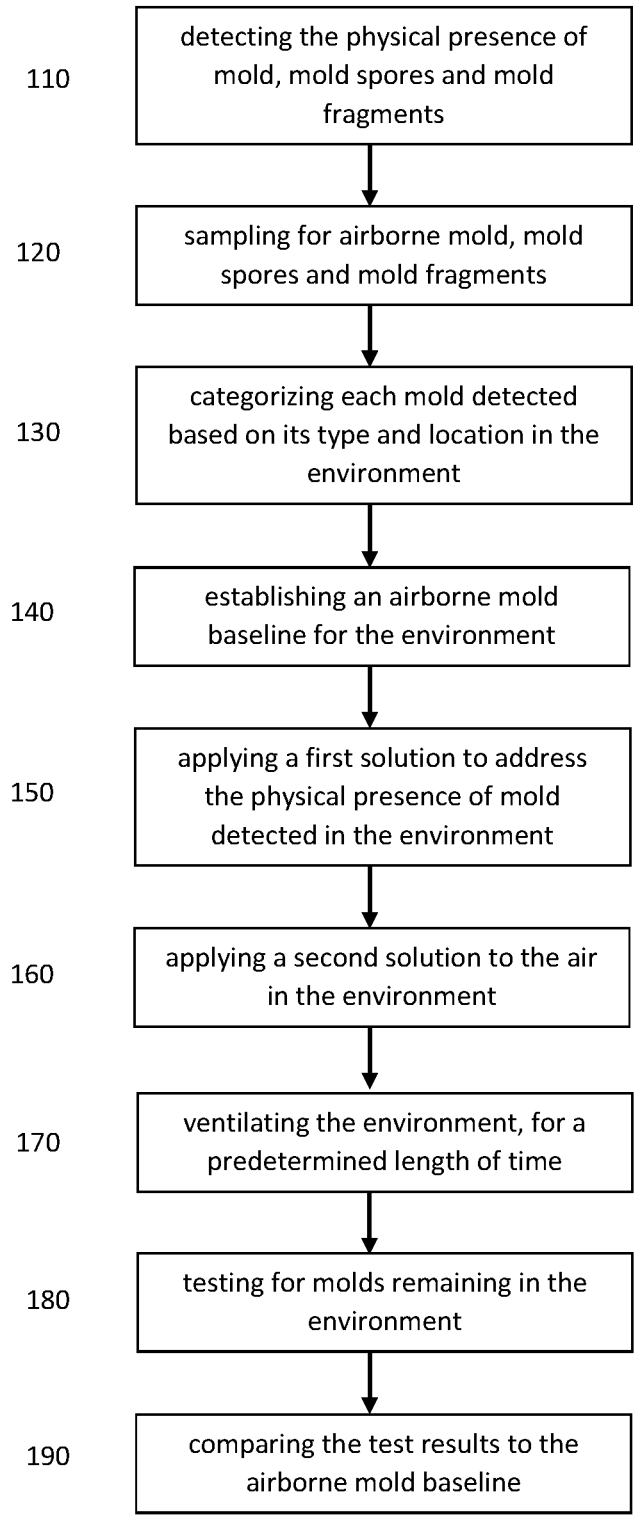

BASELINE TESTING, ANALYSIS AND TREATMENT OF AN ENVIRONMENT

CROSS REFERENCE TO RELATED APPLICATIONS

This application is a continuation of U.S. patent application Ser. No. 15/457,157, filed on Mar. 13, 2017 and now abandoned, which in turn claims priority to U.S. Provisional Patent Application No. 62/307,152, filed on Mar. 11, 2016, which is incorporated herein by reference in its entirety.

FIELD OF THE INVENTION

The present invention is generally directed toward systems and methods for remediating mold in an environment.

BACKGROUND OF THE INVENTION

Mold has become a major source of concern related to the health of individuals who live or work in an affected environment. Molds are classified as fungi, and most commonly associated with decomposing organic matter, such as underneath fallen trees and dead leaves. However, approximately 150,000 different types of molds have been identified, and are present everywhere in both indoor and outdoor environments. Molds reproduce by means of tiny spores, which will grow where there is sufficient moisture and food (organic materials such as paper, wood, cellulose, etc.). In indoor environments, mold growth is often caused by or at least exacerbated by water and/or moisture problems, which often exist in climates with above-average humidity. Although difficult to quantify with certainty, experts estimate approximately 70% of households in the United States are affected by mold.

The presence of mold may pose a serious health risk in some cases. Even small amounts of airborne mold spores may cause allergic reactions such as sneezing, runny nose, upper respiratory irritation, cough and eye irritation. Exposure to excessive amounts of mold can also cause an increase in the frequency or severity of asthma symptoms. Additionally, certain molds produce mycotoxins that can pose serious health risks to humans and animals. "Toxic mold" refers to molds which produce mycotoxins, such as Stachybotrys chartarum. Exposure to high levels of mycotoxins can lead to neurological problems and death. Prolonged exposure (for example, daily exposure) can be particularly harmful. In addition to health concerns, mold in such environments may cause structural damage by decomposing wood, drywall, carpeting and other porous building materials.

Mold in certain environments may be detectable by sight or smell, such as by observing water damage on walls or ceiling. However, mold spores can grow in places invisible to the human eye. For example, mold may be found behind wallpaper or paneling, on the inside of ceiling tiles, the back of drywall, or the underside of carpets or carpet padding. Piping in walls may also be a source of mold, since they may leak (causing moisture and condensation), and the resulting mold is undetectable to those living or working in the environment.

There presently exist certain practices and procedures for addressing mold, although each suffers from disadvantages and/or is ineffective in completely remediating the effects of mold. Currently, mold of 10 sf or more frequently involves hiring an industrial hygienist (IH) who performs a visual inspection and typically includes surface tests and air samples to assist in the preparation of a written protocol (which is often followed by a professional mold remediation company). Mold and mold remediation has become a serious enough topic to become the subject of regulation, including IICRC 5520 "Standard and Reference Guide for Professional Mold Remediation." Accordingly, mold remediation activities must be in conformance with OSHA's Standards found in Title 29 of the Code of Federal Regulations (CFR) parts 1910 and 1926.

Prior mold remediation processes are a time consuming and involve onerous tasks, often involving the removal of all mold-affected cellulosic materials (for example, drywall, wood trim, wallpaper, etc.) in the particular environment. This removal typically occurs under engineered controls of chambers and negative air pressure. In addition, personal protection equipment (PPE) is required throughout the process to protect the workers from dermal contact and inhalation of toxigenic bioaerosols produced during the remediation process, which is a further risk caused by the presence of molds. Upon completion of the remediation, an industrial hygienist returns for a visual inspection and further aerosol testing to ascertain "clearance" and certify that the property has been effectively treated and is safe for habitation. If not cleared, the process of treating mold is repeated, causing further delays and costs. Once a property is "cleared" of mold, reconstruction of the property commences to restore the property to its' previous condition. This process can take significant time to complete, and often entails significant cost. In addition, it is not always easy to detect the presence of mold spores, thereby delaying the mold remediation efforts and requiring greater effort to remove and/or treat all affected areas of an indoor environment.

Another major problem in this process is that subjective interpretations of the testing data become subjective protocols, which can and do vary greatly between different mold remediation companies. As a result, there is no true standardization protocol or "clearance" criteria. This in turn has resulted in a fragmented mold remediation market, where effective treatment in one locale may not be nearly sufficient to address the negative consequences of mold. It is with these problems and shortcomings in mind that the present disclosure in contemplated.

SUMMARY OF THE INVENTION

Given the shortcoming with the current art for addressing mold in an indoor environment, an improved system and method for remediating mold is long overdue. In addition, it is desirable to have a system and method that is determined from a standardized interpretation of mold data, follows a standardized protocol and clearance procedure, and is more effective than the current techniques used for mold remediation, and which otherwise addresses the shortcomings in prior art systems and methods.

According to one embodiment of the present disclosure, a method for assessing, remediating and testing an environment for mold is described, comprising one or more of the following steps: detecting the physical presence of mold, mold spores and mold fragments; sampling for airborne mold, mold spores and mold fragments; categorizing each mold detected based on its type and location in the environment, establishing at least one airborne mold baseline for the environment; applying a first solution to address the physical presence of mold detected in the environment; applying a second solution to the air in the environment; ventilating the environment, for a predetermined length of time; testing for molds remaining in the environment; comparing the test results to the airborne mold baseline; interpreting the comparison of the test results to the baseline; and, one or more steps are repeated until the test results are substantially the same as or improved in comparison to the baseline(s).

According to another aspect of the present disclosure, a method for remediating the effect of mold in an environment is provided, comprising the following steps: detecting the physical presence of mold, mold spores and mold fragments; sampling for airborne mold, mold spores and mold fragments; categorizing each mold detected based on its type and location in the environment; establishing an airborne mold baseline for the environment; applying a first solution to address the physical presence of mold detected in the environment; applying a second solution to the air in the environment; ventilating the environment, for a predetermined length of time; testing for molds remaining in the environment; and, comparing the test results to the airborne mold baseline.

According to another aspect of the present disclosure, a method for remediating the effect of mold in an environment is provided, which comprises the following steps: establishing a baseline for the type of environment; sampling the environment for the presence of one or more molds; applying a first solution to physical molds detected in the environment; applying a second solution to the airborne molds in the environment; ventilating the environment for a predetermined length of time; comparing the test results to the established baseline; and repeating the second through sixth steps until the test results are improved, in comparison to the baseline, by a predetermined value.

In varying embodiments, the system and method may comprise fewer or greater steps than outlined in this Summary. One having skill in the art will appreciate that embodiments of the present disclosure may be used in conjunction devices that employ automated or semi-automated manipulation. Embodiments of the present disclosure may be designed such that the system or methods described herein may be performed, for example, manually by an operator, remotely by an operator, remotely by an operator through a computer controller, by an operator using proportioning devices, or programmatically by a computer controller.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The terms "automatic", "automated" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material".

The terms "test", "determine", "calculate", and "compute," and variations thereof, as used herein, are used interchangeably and include any type of methodology, process, mathematical operation or technique.

The Summary of the Invention is neither intended nor should it be construed as being representative of the full extent and scope of the present disclosure. The present disclosure is set forth in various levels of detail in the Detailed Description, and no limitation as to the scope of the present disclosure is intended by either the inclusion or non-inclusion of steps, elements, components, etc. in this Summary. Additional aspects of the present disclosure will become more readily apparent from the Detailed Description.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below.

BRIEF DESCRIPTION OF THE DRAWINGS

The present disclosure is described in conjunction with the appended figures:

FIG. 1 is a flow chart diagram of the method in accordance with embodiments of the present disclosure.

DETAILED DESCRIPTION

The ensuing description provides embodiments only, and is not intended to limit the scope, applicability, or configuration of the claims. Rather, the ensuing description will provide those skilled in the art with an enabling description for implementing the embodiments. It should be understood that various changes may be made in the function and arrangement of elements without departing from the spirit and scope of the appended claims.

According to various embodiments described in detail herein, the present disclosure relates to systems and methods for assessing, remediating and testing an environment for mold. In one embodiment, the system and method comprises the step of making observations within the environment to detect possible evidence of mold. In this embodiment, the step may entail looking for visible mold growth in the environment, including by way of example but not limitation, mold growth occurring on structural components within the environment. In other embodiments, the systems and methods comprise looking for settled spores and/or settled dust in particular locations in the environment. Different tools and equipment described herein may be used to facilitate this observation. For example, this step may involve the use of LED flashlights as an aid for the visual inspection for mold and settled dust.

The system and method according to certain embodiments may comprise the use of specialized equipment to document the presence of any observed mold or mold spores in the environment. The documentation step may comprise the use of mobile devices, laptop computers, tablets or other electronic devices for capturing the data obtained from inspecting the environment. This step may comprise photographing the environment and/or labeling the environment in locations where mold has been observed. The photographs may be incorporated into the documentation described above or may be provided independently to the owner or operator of the environment where mold is found to exist.

The system and method according to at least one embodiment comprises the step of establishing a baseline for measuring airborne mold spores in the environment. An air sample is taken outdoors and used as a baseline to compare indoor air samples as the two environments should similarly reflect one another.

In one particular embodiment, the systems and methods comprise the use of an apparatus known as an "InstaScope®" to determine an outdoor baseline. The outdoor baseline may further comprise notation of RH, temperature, and/or geo-coded locations for results obtained by the InstaScope®. In another embodiment, the InstaScope® is used for determining the indoor air mold counts. Preferably, the InstaScope® is used to test air throughout the environment, and the results are later compared to the outdoor environment or baseline. Preferably the InstaScope® is used to conduct at least one test for every 5,000 cubic feet of indoor space in the environment. Furthermore, it is preferable to also test any HVAC system associated with the environment.

Once the data is obtained, the technician may compare data and patterns observed from the data to one or more baselines and may further describe those comparisons in documentation described above. In one example, the documentation may be an electronically stored report accessed through an electronic device, such as a tablet. In certain embodiments, the report may be exported to other users.

The system and method according to one embodiment comprises the step of testing or measuring the presence of airborne mold and/or mold spores in the environment. According to a preferred embodiment of the present disclosure, ultraviolet induced fluorescence (UVIF) is employed to detect airborne microbes and been applied to support largescale aerosol monitoring for fluorescent particles. The ability to monitor fluorescent particles (i.e. mold, bacteria and other bioaerosols) in real time on a large-scale platform removes guesswork that is currently conducted in the field and in labs. This measurement of bioaerosols also provides the necessary data to give "clearance" without bias and standardized outputs.

Portable Wideband Integrated Bioaerosol Sensors (WIBS) may also be employed to quantify the mold spores and mold fragments that are airborne in real time. Onsite, a technician obtains a baseline sample outdoors which is compared to the indoor environment testing for quantity and variation in optical and fluorescent properties. Based upon these measurements a report is created to verify that the indoor environment is light, moderate or heavily impacted with mold. Using this data along with visual inspection, a qualified technician then provides the necessary elements to standardize protocols and clearance.

According to varying embodiments described herein, the measuring or testing step may be either an alternative to or in addition to the steps of observing physical mold in the environment and may also be followed by documentation as described in greater detail above. The system and method may also comprise collecting samples of mold and/or mold spores in the environment for further analyzing. In one embodiment, the step of collection comprises the use of tape or other adhesive matter applied to the affected locations to gather samples of settled mold spores and/or settled dust in the environment.

Systems and methods of a preferred embodiment further comprise improved treatment and remediation of mold in an environment. During such treatment and remediation, it is preferred that individual technicians are protected from exposure. Such precautions may include but are not limited to the following: (PPE) Tyvek® full body suits, including hoods and boots, in accordance with 29 CFR 1910.132; respiratory protection, in accordance with 29 CFR 1910.134; and/or shoulder length polyvinylchloride gloves.

According to one embodiment, the system and method may comprise the use of sodium hypochlorite (12.5% in a preferred embodiment) combined with an amount of wetting agent or surfactant, which then may be applied to the areas in the environment affected by mold. A variety of wetting agents and surfactants may be used to achieve the desired result. In certain embodiments, different tools, equipment or techniques may be used to improve application of the proprietary sodium hypochlorite blend to nonporous and semi porous surfaces containing mold. By way of example but not limitation, such tools and equipment may comprise use of an applicator spray or misting container, microfiber towels saturated with the blend, or similar applicators.

In another embodiment, the systems and methods comprise the use of a specialized fogging apparatus to further treat the affected areas in the environment. In one embodiment, the apparatus comprises the use of submicron electrolyzed salt water (anolyte) to treat mold and mold spores in the environment. In this embodiment, the submicron electrolyzed salt water is preferably applied by use of an apparatus to create a "dry fog" or vapor, which may be applied directly to any affected areas within the environment. This form of application can occur safely and effectively to treat invisible and airborne mold and mold fragments.

In one alternative embodiment, the system and method may also comprise the use of a MAG (micro aerosol generator) to distribute one or more disinfectants throughout the environment. For example, the "NebuPure®" disinfectant may be suitable for use in such environments and distributed in a quantity determined from the total cubic footage of the environment to be treated. Other disinfectants may be used in addition to or in lieu of NebuPure®.

In one embodiment, the systems and methods comprise testing the environment, which may involve testing both structural and airborne aspects of the environment and comparing the results of the testing to the baseline step described above. The testing results may also be interpreted and/or analyzed to evaluate whether remediation has occurred in the environment. During testing, the environment may be ventilated at a rate of 1 exchange per hour or greater. In one embodiment, the ventilation may be used to achieve at least two air exchanges in the environment prior to the environment becoming occupied again. In alternate embodiments, the system and method may comprise a test for chlorine gas, such as by employing a chlorine gas meter or similar equipment.

Referring now in detail to FIG. 1, a method according to embodiments of the present disclosure is depicted. In this embodiment, the method may comprise a first step of detecting the physical presence of mold, mold spores and mold fragments 110. After the detection step 110, the method may comprise an additional step of sampling for airborne mold, mold spores and mold fragments 120. In certain embodiments, airborne mold, mold spores and mold fragments will not be of concern, and step 120 may be eliminated. In other embodiments, the method may involve sampling for airborne mold, mold spores and mold fragments 120 without detecting physical presence of mold, mold spores and mold fragments 110. The method may further comprise a step of categorizing each mold detected based on its type and location in the environment 130. Next, the method preferably comprises the step of establishing an airborne mold baseline for the environment 140. The method may additional comprise the steps of applying a first solution to address the physical presence of mold detected in the environment 150 and applying a second solution to the air in the environment 160, depending on the nature and type of mold, mold spores and mold fragments detected and sampled in the steps described above. In certain embodiments, only a first solution is applied. In other embodiments, only a second solution is applied. Next, the method may comprise the step of ventilating the environment, for a predetermined length of time 170, to either remove solution applied to the environment or allow clean air to reenter the environment, or both. The method may also comprise the step of testing for molds remaining in the environment 180 and may also comprise the step of comparing the test results to the airborne mold baseline 190. It is expressly contemplated that the sequence and number of discrete steps described in connection with FIG. 1 may be varied from the order shown in the drawing figures and described above. Additional steps are also contemplated, as reflected in the appended claims.

The system and method described herein improves the timeline for mold remediation projects from days or even weeks to complete, to mere hours. The system and method described herein also reduces costs, improves accuracy, and provides a platform for better data analysis.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

The present inventions, in various embodiments, include components, methods, processes, systems and/or apparatuses substantially as depicted and described herein, including various embodiments, sub combinations, and subsets thereof. Those of skill in the art will understand how to make and use the present inventions after understanding the present disclosure. The present inventions, in various embodiments, include providing devices and processes in the absence of items not depicted and/or described herein or in various embodiments hereof, including in the absence of such items as may have been used in previous devices or processes, e.g., for improving performance, achieving ease and/or reducing cost of implementation.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for remediating the effect of mold in an indoor environment, comprising:
    detecting the physical presence of mold, mold spores and mold fragments by inspecting structural components within the indoor environment with one or more LED flashlights;
    sampling in real time for both physical and airborne mold, mold spores and mold fragments by using adhesive tape for physical surfaces located in the environment, and air sampling cassettes, impact samplers, and Wideband Integrated Bioaerosol Sensors for airborne molds;
    capturing the mold detected or sampled in the indoor environment by use of an electronic device;
    documenting the presence of both physical and airborne mold captured by the electronic device;
    categorizing each mold detected based on its type and location in the indoor environment by photographing and labeling each mold, mold spore or mold fragment detected or sampled;
    establishing a first baseline relating to an outdoor environment, the first baseline comprising a physical mold baseline and an airborne mold baseline;
    establishing a second baseline relating to the indoor environment, the second baseline comprising a physical mold baseline and an airborne mold baseline;
    applying a first solution to address the physical presence of mold detected in the indoor environment, wherein the first solution comprises at least sodium hypochlorite 12.5% and a surfactant selected from the group consisting of alcohol ethoxylates;
    applying a second solution to the air in the indoor environment, wherein the second solution comprises a fog-based, electrolyzed salt water solution having particle size less than 1 micron;
    ventilating the indoor environment, for a predetermined length of time determined from the first baseline and the second baseline, wherein the step of ventilating occurs at a rate of about 1 to 3 exchanges per hour;
    disinfecting the indoor environment by use of a micro aerosol generator to distribute one or more disinfectants throughout the indoor environment;
    testing at least once for every 5,000 cubic feet of space in the indoor environment for molds remaining in the indoor environment to determine an updated second baseline; and
    comparing the test results and the updated second baseline to the first baseline.

2. The method of claim 1, wherein the first and second baselines include RH, temperature and geo-coded locations in the outdoor environment and indoor environment, and further comprises the step of interpreting the comparison of the test results to both the first baseline and the second baseline.

3. The method of claim 1, wherein the steps of detecting, sampling, categorizing, applying a first solution, applying a second solution, ventilating the indoor environment, and testing for molds are repeated until the updated second baseline is substantially the same as the first baseline.

4. A method for remediating the effect of mold in an indoor environment, comprising:
    establishing a first baseline relating to an indoor environment, the first baseline comprising a physical mold baseline and an airborne mold baseline;

establishing a second baseline relating to an outdoor environment, the second baseline comprising a physical mold baseline and an airborne mold baseline;

detecting the physical presence of mold, mold spores and mold fragments by inspecting structural components within the indoor environment with one or more LED flashlights;

sampling in real time the indoor environment for the presence of one or more airborne molds;

capturing the mold detected or sampled in the indoor environment by use of an electronic device;

documenting the presence of both physical and airborne mold captured by the electronic device;

applying a first solution to physical molds detected in the indoor environment;

applying a second solution to the airborne molds in the indoor environment;

ventilating the indoor environment for a predetermined length of time;

obtaining mold test results for at least every 5,000 cubic feet of space in the indoor environment;

comparing the test results to the first baseline and the second baseline;

establishing an updated first baseline from the test results obtained and the comparison of the test results to the first and second baselines; and repeating the sampling, applying a first solution, applying a second solution, and ventilating and obtaining mold test result steps until the mold test results are improved, by comparing the updated first baseline to the second baseline, until the updated first baseline is in proximity to the second baseline by a predetermined value.

5. The method of claim 4, wherein the first solution comprises sodium hypochlorite 12.5% in combination with at least one surfactant.

6. The method of claim 4, wherein the second solution comprises electrolyzed salt water having particle size less than 1 micron.

7. The method of claim 4, further comprising the use of a micro aerosol generator to distribute one or more disinfectants throughout the environment.

8. A method for remediating the effect of mold in an indoor environment, comprising:

detecting the physical presence of mold, mold spores and mold fragments by inspecting structural components within the indoor environment with one or more LED flashlights;

sampling in real time for both physical and airborne mold, mold spores and mold fragments using adhesive tape for physical surfaces located in the environment, and air sampling cassettes, impact samplers, and Wideband Integrated Bioaerosol Sensors that quantify airborne mold spores and mold fragments;

capturing the mold detected or sampled in the indoor environment by use of an electronic device;

documenting the presence of both physical and airborne mold captured by the electronic device;

categorizing each physical and airborne mold detected based on its type and location in the indoor environment;

establishing an airborne mold baseline associated with the indoor environment;

establishing a physical mold baseline associated with the indoor environment;

establishing an airborne mold baseline associated with an outdoor environment;

establishing a physical mold baseline associated with an outdoor environment;

applying a first solution to address the physical presence of mold detected in the indoor environment;

applying a second solution to the air in the indoor environment;

ventilating the environment, for a predetermined length of time;

disinfecting the indoor environment by use of a micro aerosol generator to distribute one or more disinfectants throughout the indoor environment;

testing for molds remaining in the indoor environment, wherein the testing comprises at least one independent test for every 5,000 cubic feet of space in the indoor environment; and comparing the test results to the baselines associated with the indoor environment and the outdoor environment;

wherein the baselines each include RH, temperature and geo-coded locations in the respective outdoor and indoor environments.

9. The method of claim 8, wherein the first solution comprises at least sodium hypochlorite 12.5% and a surfactant.

10. The method of claim 9, wherein the surfactant is selected from the group consisting of alcohol ethoxylates.

11. The method of claim 8, wherein the second solution comprises a fog-based, electrolyzed salt water solution having particle size less than 1 micron.

12. The method of claim 8, wherein the categorizing comprises photographing and labeling each mold, mold spore or mold fragment detected.

13. The method of claim 8, wherein the step of ventilating occurs at a rate of about 1 to 3 exchanges per hour.

14. The method of claim 8, wherein the step of testing comprises employing ultraviolet induced fluorescence (UVIF) to detect airborne mold, and further comprises testing an HVAC system associated with the indoor environment.

15. The method of claim 8 further comprising the step of generating a report comprising a comparison of data captured by the electronic device and the test results to the first baseline and the second baseline.

* * * * *